United States Patent
Cinqualbre et al.

(10) Patent No.: US 8,688,476 B2
(45) Date of Patent: Apr. 1, 2014

(54) INTEROPERABILITY TOOLS AND PROCEDURES TO AGGREGATE AND CONSOLIDATE LAB TEST RESULTS

(76) Inventors: Jacques Cinqualbre, Rosheim (FR); Fabrice Papst, Strasbourg (FR); Nicolas Grosse, Strasbourg (FR); Medy Benzeghba, Sarreguemines (FR)

(*) Notice: Subject to any disclaimer, the term of this patent is extended or adjusted under 35 U.S.C. 154(b) by 0 days.

(21) Appl. No.: 12/969,124

(22) Filed: Dec. 15, 2010

(65) Prior Publication Data

US 2011/0257998 A1 Oct. 20, 2011

Related U.S. Application Data

(60) Provisional application No. 61/286,609, filed on Dec. 15, 2009.

(51) Int. Cl.
*G06Q 50/00* (2012.01)
*G06Q 10/00* (2012.01)

(52) U.S. Cl.
USPC .................................................. 705/3; 705/2

(58) Field of Classification Search
USPC .......................................................... 705/2–3
See application file for complete search history.

(56) References Cited

U.S. PATENT DOCUMENTS

| | | | |
|---|---|---|---|
| 6,018,713 A * | 1/2000 | Coli et al. | 705/2 |
| 2001/0014769 A1* | 8/2001 | Bufe et al. | 600/300 |
| 2002/0198739 A1* | 12/2002 | Lau et al. | 705/3 |
| 2004/0186821 A1* | 9/2004 | Matson et al. | 707/1 |
| 2007/0016440 A1* | 1/2007 | Stroup | 705/2 |
| 2008/0201172 A1 | 8/2008 | McNamar | |
| 2008/0208633 A1* | 8/2008 | Navani | 705/3 |
| 2009/0110192 A1* | 4/2009 | Elrod et al. | 380/44 |

OTHER PUBLICATIONS

Rolke, Quantitative sensory testing in the German Research Network on Neuropathic Pain (DFNS): Standardized protocol and reference values, Aug. 2006, PAIN, vol. 123, Issue 3 pp. 231-243, ISSN 0304-3959.*

* cited by examiner

*Primary Examiner* — Tran Nguyen
(74) *Attorney, Agent, or Firm* — Osha Liang LLP

(57) ABSTRACT

A method for displaying correlated data of a patient includes receiving, using a hardware processor, incoming lab test data at a central server. The incoming lab test data includes a plurality of different original formats and is stored on the central server in the original formats received. The lab test data is then converted into a unified format to obtain unified format lab test data. The unified format lab test data is then correlated, using the hardware processor, based on a healthcare identification code to obtain correlated data and is displayed as a single document.

36 Claims, 7 Drawing Sheets

FIGURE 4

| LabCode | LOINC |
|---|---|
| 93f4ee3a17b83aaff6968b955ffa53e5 | 29765-5 |
| 69b8c94915568eb69641e246b6aec4c0 | 14800-7 |
| cec3e1c4e7705ef016511ac490a904ca | 713-8 |
| 8864438bde14e10855d819d0a00066b7 | 14646-4 |
| 07eab425a3a7c066d34d9039ff8852d4 | 3218-5 |
| 975eed1e189697f3d1bc7c8c6d6769ce | 786-4 |
| 273e9ca91470e2e6f2a4faad340c6f29 | 5905-5 |
| 3b325ef6418f0e546b2d26ca2b04b669 | 2711-0 |
| 6fba3c38d7c3a45dd716bd0fc8dd91c1 | 14682-9 |
| b2f6d8f64d581f99a32d57e185856ab6 | 14933-6 |
| 71260c707f2dcc782b59abd7e3052ac1 | 14684-5 |
| 60421be1a2358da773323a4d84140393 | 16128-1 |
| 2648fa1fc807d595aeb152b1f8bd6412 | 22664-7 |
| cf6cc48584c6cd72b11431eb0a90b686 | 2324-2 |
| 2576db93b4ecaa7396851a54027ac295 | 53763-9 |
| 3e300d48bd8ff47611739ff2f72a6928 | 14631-6 |
| 416ce7525ad50a50f876e6624ee6b551 | 2075-0 |
| b01e9fde712c4a204be705f3514f8bb4 | 20453-7 |

Data as Hashed
400

Data in LOINC
402

FIGURE 5A

| LAB TESTS | | | | | | ⊞ |
|---|---|---|---|---|---|---|
| First date 13/11/07 | Last date 08/12/09 | Labs 2 | | Tests 12 | | |
| | | | 11/13/07 | 02/12/08 | 04/16/08 | |
| BLOOD CHEMISTRY | | | | | | |
| SGPT (ALT) (U/l) | [21] | | 14 | 15 | 20 | |
| BUN (mmol/l) | [10.16] | | 15.1 | 9.4 | 11.18 | |
| Protein (g/l) | [81] | | 73 | 75 | 76 | |
| Phosphorus (mmol/l) | [0.95] | | 0.88 | 0.85 | 1.24 | |
| CK (U/l) | [288] | | From: HCC Colmar Normal value: 1 - 1.45 | | 300 | |

| LAB TESTS | | | | | | ⊞ |
|---|---|---|---|---|---|---|
| First date 13/11/07 | Last date 08/12/09 | Labs 2 | | Tests 12 | | |
| | | | 11/13/07 | 02/12/08 | 04/16/08 | |
| BLOOD CHEMISTRY | | | | | | |
| SGPT (ALT) (U/l) | [21] | | 14 | 15 | 20 | |
| BUN (mmol/l) | [10.16] | | 15.1 | From: CHU Strasbourg Normal value: 10 - 49 | | |
| Protein (g/l) | [81] | | 73 | 75 | 76 | |
| Phosphorus (mmol/l) | [0.95] | | 0.88 | 0.85 | 1.24 | |
| CK (U/l) | [288] | | | | 300 | |

501   510   512   514   505

INTEROPERABILITY TOOLS AND PROCEDURES TO AGGREGATE AND CONSOLIDATE LAB TEST RESULTS

CROSS-REFERENCE TO RELATED APPLICATIONS

The present application claims benefit of U.S. Provisional Patent Application 61/286,609, filed Dec. 15, 2009. The contents of the provisional application are hereby incorporated by reference in their entirety.

BACKGROUND OF THE DISCLOSURE

1. Field of the Disclosure

The present invention relates to electronic health records, and in particular to electronic lab test records and providing interoperability when the electronic lab test records are in different formats.

2. Description of the Related Art

A reliable and secure transmission of data between a lab and a laboratory information system ("LIS") and then from the LIS to a care practitioner (doctor, nurse, etc.), all within a particular institution, is commonly employed in the healthcare field. For a period of time, such data transmission was limited to transferring a "picture" of the document. However, today, electronic transfer of data is the norm inside an institution. Within an institution, the client (care provider) may execute or employ a single program allowing electronic exchange of data, but may be restricted to staying within the closed institutional system, thus forming the LIS. Outside this limited circle, export of lab results is achieved only by sending an electronic PDF, sending a physical copy by postal service, or by facsimile. The different formats precludes integration of the data into a spreadsheet allowing comparisons over time. In order to achieve a single spreadsheet or document containing results from different laboratories, manual intervention for entry and reconciliation of the data is typically required.

In view of the above, with an increasing frequency, a patient may carry physical copies of lab test results performed by different healthcare providers between the various care providers for review by a healthcare professional, and, therefore, the physical copies cannot be displayed on a common platform with data obtained within a hospital. Further, when a patient seeks lab tests performed by an outside facility, the format and/or platform may be different from the format and platform of the in-house laboratory or LIS.

For example, an anaesthesiologist in charge of a pre-op outpatient consultation may read the lab test results on a paper form brought by the patient or transmitted directly from an outpatient laboratory. The lab results may be provided by fax or through electronic format, such as a PDF image, and usually will be printed in the office of the outpatient doctor. Even if electronic transmission of in-house lab test results are provided to the doctor, there is commonly some incompatibility with the results of the test performed outside of the hospital. In this case, it may not be feasible to display results from various facilities in a single format for the healthcare provider to use.

Furthermore, as far as chronic patients are concerned, the situation is even worse. Frequent back-and-forth transfers and orders (different lab tests) occur in the scope of shared follow-up among a highly specialized tertiary center and a local physician (family, general practitioner, etc.). Accordingly, a high volume of transfer of lab test results may be seen in both directions, from the tertiary center to the local physician, and vice versa. The same limitations described above remain. Thus, it is typically not feasible to consolidate the results of both sources automatically on a single electronic spreadsheet. A similar result occurs in collaborative diagnosis, where different actors cannot reconcile their own lab test results with the results of other members of the collaboration.

Clinical assessment, for example in the above approaches to healthcare, benefits from an ontological approach which, in the first half of the 20th century, lead to classify diseases (evolutionary classifications "ICD", current version #10) and to enhance searches by using significant wording (SNOMED being the most popular among numerous vertical applications). However, these solutions of providing a common language have limitations. As far as clinical data are concerned, taxonomy of symptoms or diseases is directed to a discouraging exhaustiveness for the end-user, as there are several hundreds of thousands references in SNOMED.

As far as biology is concerned, a standard has emerged with Health Level 7 (HL7). HL7 is an organization involved in the development of international standards in healthcare. It provides a framework and related standards for the exchange, integration, sharing, and retrieval of electronic health information. These data standards are meant to permit healthcare providers to share clinical information efficiently. Within HL7, there are, for example, conceptual standards (HL7 RIM), document standards (HL7 CDA), application standards (HL7 CCOW), and messaging standards (HL7 v2x and v3 series). The current versions of HL7 in use include HL7 2.5 and HL7 3.0, the latter integrating a bridge with the Digital Imaging and Communications in Medicine format. The European version, named HPRIM, although in use, is being phased out because partial conversion between formats is easily achieved.

Even with the advent of HL7, the above described compatibility issues, and limitations within a single institution, arise, in part, from the existence of an additional layer. In addition to the standards just described, there arises a problem with use of vocabulary, even within the single HL7 format. For instance, in lab results, "red blood cell" may be described under ten or so different representations as well as homonyms, synonyms, and/or acronyms, namely: Red Blood Cell(s), Red blood cell(s), red blood cell(s), Erythrocyte(s), erythrocyte(s), Hemocyte(s), hemocyte(s), RBC, Rbc, and Red BC, among others. Furthermore, legacy versions and non-complying formats also exist and are in use.

SUMMARY OF THE CLAIMED SUBJECT MATTER

A method for providing interoperability of laboratory records of a patient is provided. The method includes receiving, using a hardware processor, incoming lab test data at a central server. The incoming lab test data includes a plurality of different formats and is stored on the central server in the formats received. The lab test data is then converted into a unified format to obtain unified format lab test data. The unified format lab test data is then correlated using the hardware processor, based on a healthcare identification code to obtain correlated data and is recorded, using the hardware processor, into a single document.

BRIEF DESCRIPTION OF DRAWINGS

Features of the present disclosure will become more apparent from the following description in conjunction with the accompanying drawings.

FIG. 4 is an exemplary correlation chart in accordance with embodiments of the present disclosure.

FIGS. 5A and 5B show exemplary outputs of correlated lab test data in accordance with embodiments of the present disclosure.

DETAILED DESCRIPTION

Figure 1:
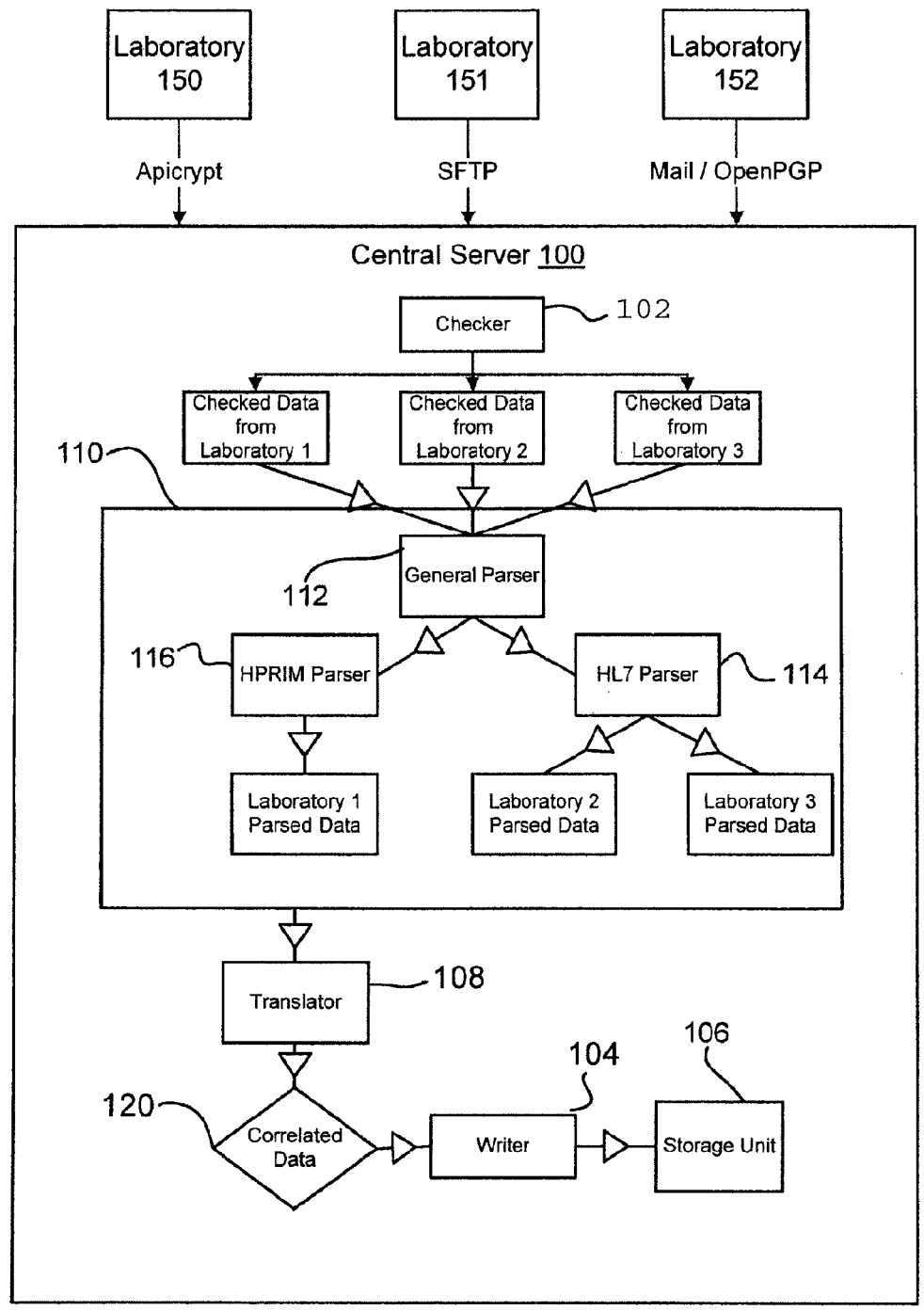
FIG. 1 is schematic of processes in accordance with embodiments of the present disclosure.

Embodiments of the present invention are explained below, referring to the attached figures. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

In view of the above, a system for interoperability of lab test results is provided. Interoperability may be designed to produce a single usable spreadsheet or other consolidated reference document. Interoperability, at the individual/patient level, allows for connected and structured aggregation of laboratory (lab) test results collected from different sources, in different formats, and reconciling the results into a single format and/or document.

Embodiments disclosed herein are directed to automatic (or semi-automatic) aggregation of lab test results processed from human material, especially blood, by clinical laboratories and/or other healthcare providers. As used herein, a healthcare provider may include doctors, nurses, technicians, clinics, hospitals, laboratories, and any other individuals and institutions that provide healthcare to patients.

Further, embodiments disclosed herein allow for reconciliation of the disparate format and language variations, and produce a single, comprehensive result. As such, embodiments of the invention are directed to collecting and correlating structured data, thereby preventing a "piling" process of independent documents—simple grouping of images, such as PDFs. Embodiments of the invention provide for "ex-post" interoperability, through a reconciliation process of documents and/or results produced at different laboratories. Embodiments disclosed herein may also provide a reconciliation process for heterogeneous documents in terms of taxonomy, units, normal values, sample volumes, and/or parameters, thereby allowing an automatic integration of the laboratory data.

Generally, embodiments of the invention allow for a secure server to store and process laboratory data. A healthcare provider may securely connect to the server and upload lab test results. The lab test results may be uploaded in any format—there is no requirement that a particular format be used. The server may then process the lab test results and convert the lab test results into a unified format, creating unified format lab test data. This process may be repeated with many different laboratories, each using a different format when submitting or sending the lab test data to the server. The server may convert all of the data, from the different laboratories, into the unified format. Once the data is in the unified format, the server may correlate, based on a healthcare identification code, the unified format lab test data to obtain correlated data. The correlated data may then be entered into and/or used to create a single document, such as a spreadsheet or other reference document.

Advantageously, the above process may be used for a single patient, over the course of a treatment or their life. However, in order to enable a secure system based on a single individual, a unique identifier may be required for each individual patient.

Accordingly, the first step in building an electronic health record (eHR) is to secure a reliable identification ("ID") that all participants in the health care process may use either to input data onto the eHR or to read the contents of the eHR, thereby associating an eHR with a particular patient. One example of an identification that may be used is a regular ID (based on last name, first name, birth date, social security number, etc.). Alternatively, when a patient belongs to a health plan, an ID may be provided internally with special procedures to "break the glass" if necessary when the patient is seen by a provider outside of the network. For instance, Kaiser Permanente, a healthcare provider and health plan, has developed its own internal system for assigning identifiers to patients and/or customers. Some governmental agencies, for example in Nordic European countries, Canada, and France, have developed specific national policies and/or personal identification rules, procedures, and/or schemes for assigning identifiers to individuals, citizens, patients, and/or customers.

As an example, in France, the Commission Nationale Informatique et Libertés, in charge of protecting the individual in the IT world opposed the use of the "NIR" (social security number), and Agence des Sysytèmes d'Information Partagée en santé has established a procedure using the social security number, the birth date, and a digital transformation of the first name, combined through a specific algorithm, to produce an "INS-C" (Identifiant National Santé-Calculé) resulting in a 22 digit number.

The goal of the aforementioned entities, or any other unique identification scheme, in part, is to protect the individual from intrusive viewers of the patient's medical profile and/or record. However, one major limitation to these proposed ID schemes is that there may be no value outside of the territory, institution, company, policy, etc. that assigns the unique identification number.

Accordingly, an alternative approach may involve combining the classical approaches described above with a personal URL for each individual's health record. Moreover, this process may be used to assign a URL for any resource in healthcare—providers, institutions, etc. Allocating a permanent URL to the individual could be prolonged by appending an internal numbering system to the domain name and subsequently communicating the URL widely to all involved care providers without impairing the security protected by a thorough access policy and passage tracking.

The URL approach may allow for an easy and simple distribution model for different healthcare providers involved in creation of a patient's eHR. The format is easy to use and may allow for storing of sub-records among stakeholders of the eHR. Furthermore, the unique identification based on a URL may allow for security in eHR and compliance with HIPAA and/or other rules, regulations, and/or laws governing the handling of patient health records, and electronic health records in particular.

A unique identifier allows for a normative approach to eHR. If a patient has a unique ID, any records, regardless of format, maybe provided to a central server, and converted and/or correlated into a single reference document, including all of the pertinent information of the patient, thereby allowing interoperability between different sources of lab test data. By providing interoperability of patient records, assigned to the unique ID, a longitudinal record of the patient to be created.

Now referring to FIG. 1, a schematic diagram of a system in accordance with one or more embodiments of the invention is described. External laboratories (laboratory 150, laboratory 151, and laboratory 151) may be configured to send lab test data collected at the respective laboratories to a central server 100. The laboratories 150, 151, and 152 may be blood or other medical test laboratories, including hospitals, configured to collect samples and data from patients.

The different laboratories 150, 151, and 152 may send the lab test data by different methods. For example, laboratory 150 may send the lab test data collected at laboratory 150 by Apicrypt. Laboratory 151 may send the lab test data collected at laboratory 151 by secure FTP transfer. Laboratory 152 may send the lab test data collected at laboratory 152 by secure e-mail or OpenPGP. Further, those skilled in the art will appreciate that other secure or non-secure means may be used to send electronic data from a laboratory to the central server 100.

The central server 100 may include one or more hardware processors and one or more storage devices. Further, although shown as a single server and storage unit, central server 100 may include multiple servers, the processing and storage, described herein may occur on separate and distinct hardware, redundancies may be provided, mirror images created, and/or other processing and storage methods may be used without departing from the scope of the present invention. Moreover, although only three laboratories are shown, those skilled in the art will appreciate that any number of laboratories may provide data to the central server 100. Further, central server 100 may be a computer system as shown and described with reference to FIG. 7.

The central server 100 may include a checker 102, a writer 104, a storage unit 106, one or more parsers 110 (112, 114, and 116), and a translator 108. Further, those skilled in the art will appreciate, that although central server 100 is shown with the noted features, central server 100 may include one or more of each of the hardware and/or software devices described herein, and/or may include other elements known in the art. Further, central server 100 may include more than one physical unit and/or may be contained in multiple units, without departing from the scope of the present invention.

The checker 102 may be configured to sort the incoming laboratory data. The checker 102 may be a hardware processor or may be a computer program. The checker 102 may be configured to remove information within the incoming data associated with the transport of the data. Accordingly, the checker 102 may be configured to distill the incoming laboratory data to only leave the pertinent lab test data.

The writer 104 may be a writing program and/or hardware processor that may write data to a storage unit and/or between other elements and/or hardware processors of the central server 100. The writer 104 may be configured to write data to the storage unit 106 that may be any memory storage unit known in the art.

The central server 100 may include one or more parsers 110. A general parser 112 may be configured to parse any incoming information and/or distribute the incoming data to other parsers. For example, data that is in an HL7 format may be sent to parser 114. The parser 114 may be configured to parse data in the HL7 format, and may be configured to assign a dictionary to the data in the HL7 format, so that the data may be translated, as described below. The parser 116 may be configured to parse data that is formatted in HPRIM format. Although only three types of parsers 110 (112, 114, and 116) are shown, those skilled in the art will appreciate that more or fewer parsers may be included in the central server 100. In particular, parsers dedicated to the different versions of HL7 and/or HPRIM and/or dedicated to other known formats/norms may be provided to more efficiently parse the lab test data without departing from the scope of the present invention.

The parsers 110 may assign a dictionary to each format, such as HL7 and HPRIM. The dictionary may provide a correspondence table between the HL7 format, or the HPRIM format, and a generic format, such as logical observation identifier names and codes ("LOINC"). Further, the parsers 110 may be configured to hash the original format (HL7, HPRIM, etc.) and produce a hashed data that may be assigned a dictionary.

The translator 108 may be configured to translate the data from the original format (HL7, HPRIM, etc.) to the generic format (e.g., LOINC) using the assigned dictionaries. For example, the translator may be configured to translate, using an assigned dictionary, a hashed data set into LOINC. The translator 108 may be configured to correlate the data from the various laboratories and generate correlated data 120, thereby incorporating each of the data sets into a single document. The correlated data 120 may be a complete health record for a particular patient or may be a single data set over a period of time or from particular laboratories, or may be any other data set.

Figure 2:
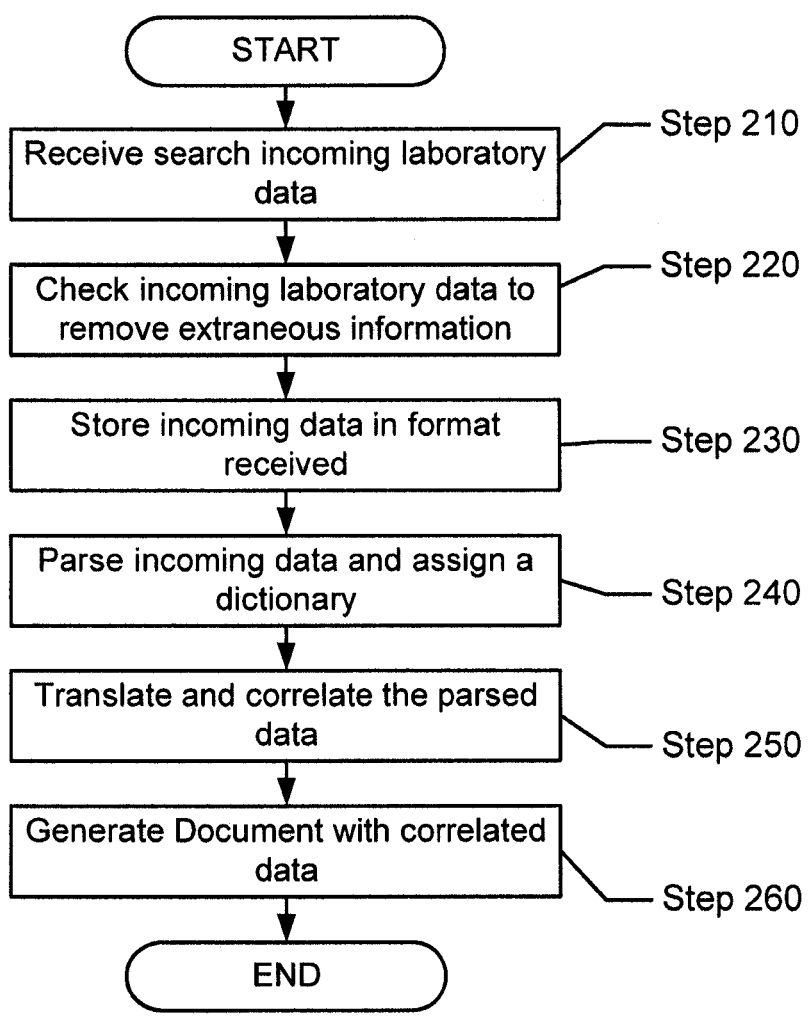
FIG. 2 is a flow chart of processes in accordance with embodiments of the present disclosure.

Now, with reference to FIG. 2, a process of generating the correlated data of a patient will be described. Initially, at step 210, laboratories may send lab test data to a central server to be processed. The central server may receive the data at a remote location with respect to the source laboratories. To enable a secure transportation of medical data, for example, Apicrypt (which is a secured messaging system using encrypted electronic mail based on a registry of partners among care providers, including a private key) may be used. Alternatively, other secure electronic transfer methods may be used.

For example, a lab may securely connect to a server. When joining or connecting to the server, the lab may use a virtual private network, or other secure connection. The lab, once connected, may then transfer the lab test data to the server by a secure messaging system, such as Apicrypt, mentioned above. Although Apicrypt is mentioned here, those skilled in the art will appreciate that other encryption tools may be used without departing from the scope of the present invention.

Moreover, although a virtual private network is described as the means of connecting to a server, those skilled in the art will appreciate that other secure connection methods may be used without departing from the scope of the present invention. For example, secure messaging systems, secure electronic e-mail, FTP, FTPS, secure web services, and/or any other secure and/or encrypting method or process known in the art may be employed without departing from the scope of the invention. The process, as disclosed herein, does not rely on a single transportation format and/or method and, therefore, any and all formats and methods of transportation of data may be used.

Next, at step 220, the incoming laboratory data may be checked. Because the different laboratories may send the lab test data by different means and/or methods, the checking function removes the information associated with the transportation of the data, leaving only the pertinent lab test data. No extraneous data, such as address and/or protocol data, may be part of the lab test data after the checking function is complete.

Next, at step 230, the lab test data, after being checked, may be stored. The stored lab test data, at step 230, may be raw and unprocessed data, other than the removal of the transportation and/or protocol data. Accordingly, a copy of the original data, prior to processing, may be stored.

Next, at step 240, the lab test data may be parsed. During parsing at step 240, the lab test data may be assigned a dictionary associated with a particular format of the lab test data. A dictionary may provide a data set of equivalents that may include a label-plus-unit conversion allowing translation to a generic and/or arbitrary code.

Further, in accordance with embodiments of the invention, the lab test data may be hashed when it is parsed. For example, a hash function and/or algorithm may be employed. The hash function may extract information about the patient and/or originating laboratory, the code of the lab test results, and units and/or other optional and/or desired information. Further, those skilled in the art will appreciate that other information, and/or combinations of other information may be used and/or extracted during the hash function, without departing from the scope of the invention. Accordingly, at step 240, the incoming lab test data may be parsed, hashed, and assigned a dictionary that may enable translation of the data from the originally received format to a generic format.

The parsing function may allow for reconciliation and conversion of disparate formats of lab test data to be correlated and aggregated into a single usable format regardless of delivery method or formatting of the lab test data. The basic principle is that nothing has to be imposed on the labs when the lab test data is provided to a central server; there is no requirement of a specific format and no requirement of a particular transfer protocol (other than those requirements imposed by rule, regulation, and/or law). Accordingly, embodiments of the invention allow all laboratories to maintain the current software and/or protocols employed by the laboratories, and imposes no changes on internal systems.

Next, at step 250, the parsed data, that may have an assigned dictionary, may be translated into the generic format. The generic format data may then be translated into a universal language, such as a healthcare identification code, or, more specifically, logical observation identifiers names and codes (LOINC), using the appended dictionary. Accordingly, a correspondence table may be created between the hashed data and the LOINC. Accordingly, the dictionaries may provide a translation for a hashed function of a standard format, such as HL7 or HPRIM, into LOINC. The translated data may be correlated to form correlated data.

Figure 3:
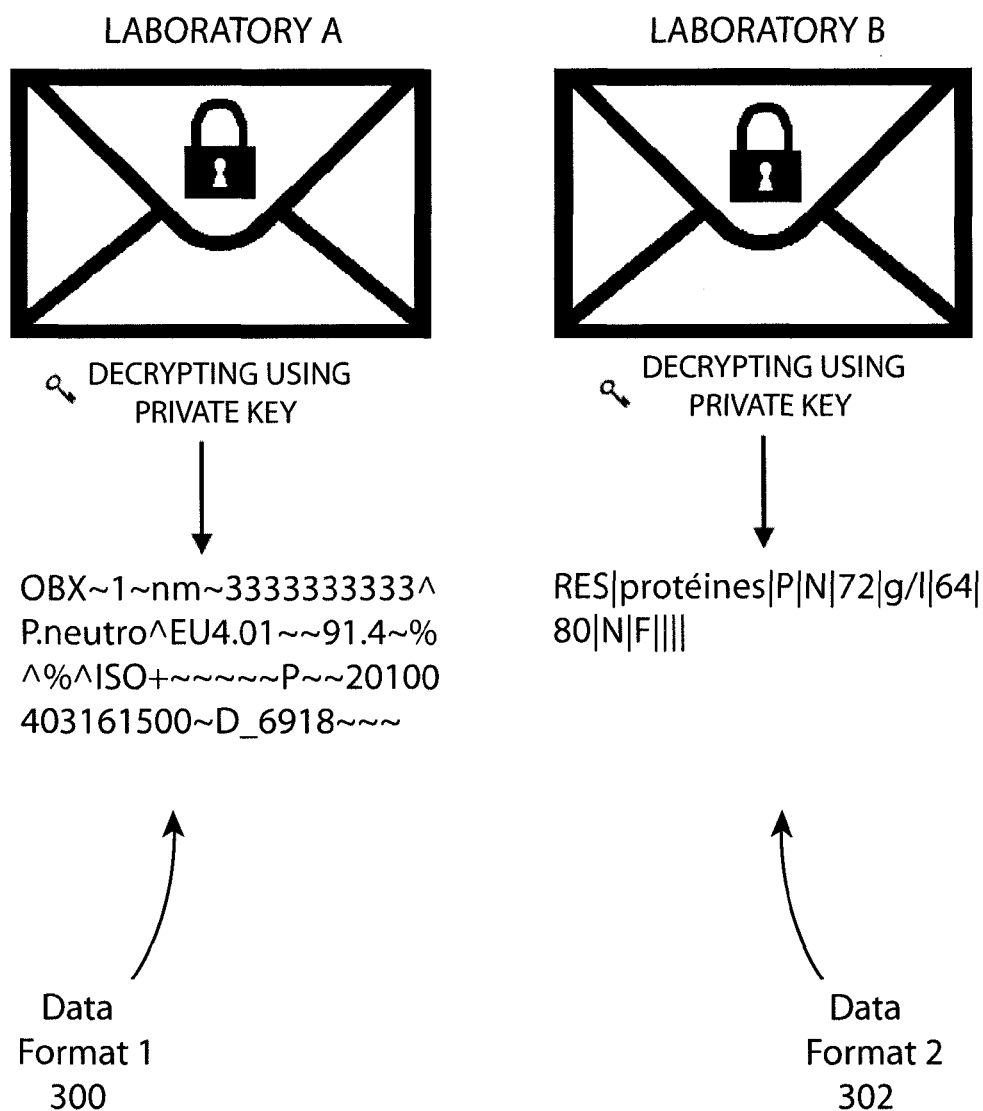
FIG. 3 is a representation of disparate incoming lab test data.

For example, data may be provided in HL7 format. Per HL7, any line announcing a coded result will start with "OBX," the elements are separated by pipes "|", and sub-splitting may be designated by "^" or "~." In contrast, data provided in the HPrim format announces a coded result with "RES," and only pipes "|" are used for separation. Further, there are different versions of HL7 and HPrim, and, moreover, not all laboratories conform to these two formats, and so other formats may be provided to the central server. As shown in FIG. 3, Laboratory A may provide lab test data in data format 1, HL7, and Laboratory B may provide lab test data in data format 2, HPrim.

In order for proper compatibility and/or interoperability to occur, the incoming lab test data may need to be converted into a usable and consistent format. Accordingly, the lab test data may be transformed generically into Java script object notation. To convert into Java script object notation from the multiple formats, a unique code or test may be provided that serves to convert the lab test data. As such, the central server may include a reference list that provides a conversion table for each of the incoming formats to convert to Java script object notation.

Finally, at step 260, the correlated data may be employed to generate a single document. Once the data is converted to LOINC, it may be written into a single unified, correlated data set. The single document may be a file, spreadsheet, text, or other electronic format that may include all of a patient's information, as collected from a variety of sources.

Now referring to FIG. 3, an example of different incoming formats from laboratories is shown. Laboratory A may provide data with an encryption using a private key that may be in data format 300. Data format 300 may be HL7. Laboratory B may provide data with an encryption using a private key that may be in data format 302. Data format 302 may be HPRIM. Accordingly, FIG. 3 shows different laboratories providing lab test data in different formats.

Now referring to FIG. 4, an example of a correspondence table is shown. Lab test data may be hashed from an original format, such as HL7 or HPRIM, and converted into a hashed data set 400. The hashed data set 400 may be provided with a correspondence and/or translation to data in LOINC format 402. Accordingly, in accordance with one or more embodiments of the invention, a correspondence chart, or dictionary, may be provided to convert any format into a generic format.

Once the process described herein is complete, a bridge may be used for external parties, such as a healthcare provider, to access the correlated unified format lab test data and/or text file. The bridge may use an association table related to the unique identification number of a given patient, as discussed above, to share the data between the healthcare providers that may need access to the lab test data. In order to obtain the data, the institution may be equipped with a derivative of the parser application. The derivative of the parser function, on the institution-side, has a single parser function, instead of the multiple parsers for each of the widely used formats and a general parser. The single parsing function of the derivative parser application will transform the unified format lab test data sent by the bridge into usable data for the requestor to use and/or observe.

Following parsing and correlations, an operative function may allow for display and use of the data in a synthetic individual-oriented, or patient-oriented, spreadsheet. The results are displayed under differentiable graphical characters (e.g., different fonts, italics, underlining, etc.). Moreover, corresponding units and/or results may appear as metadata when selecting a parameter and will also be available on graphs. In general, results are expressed in a structured manner using adjacent columns in the operative function.

For example, with reference to FIGS. 5A, 5B, 6A, and 6B, a sample data set as produced by the operative function is shown. FIGS. 5A and 5B show data tables 500 and 501, respectively, with data acquired from two or more laboratories. Both FIGS. 5A and 5B show the same data entries in the tables 500 and 501, but with an indication that more than one laboratory provided the data, one lab's data set is underlined, another lab's data set is not underlined. As shown in the tables, columns with underlined data entries are provided from the Laboratory HCC Colmar (FIG. 5A showing pop-up 504 of this lab on table 500), and data entries that are not underlined are provided from the Laboratory Labo CHU Strasbourg (FIG. 5B showing pop-up 505 of this lab on table 501). When viewing the information, a healthcare provider may see from which laboratory the data was received from, and also observe the data entries (or values) over time.

Furthermore, as shown in FIGS. 5A and 5B, first column 510 may provide the particular lab test that a data entry represents, such as cholesterol, triglycerides, glucose, sodium, red blood cell count, platelets, etc. The next entry 512 in the table may be shown in brackets "[ ]" and may represent the most recent values for a particular patient. Also represented are a series of columns 514 displaying the patient's results over time, from each of the laboratories.

Figure 6A:
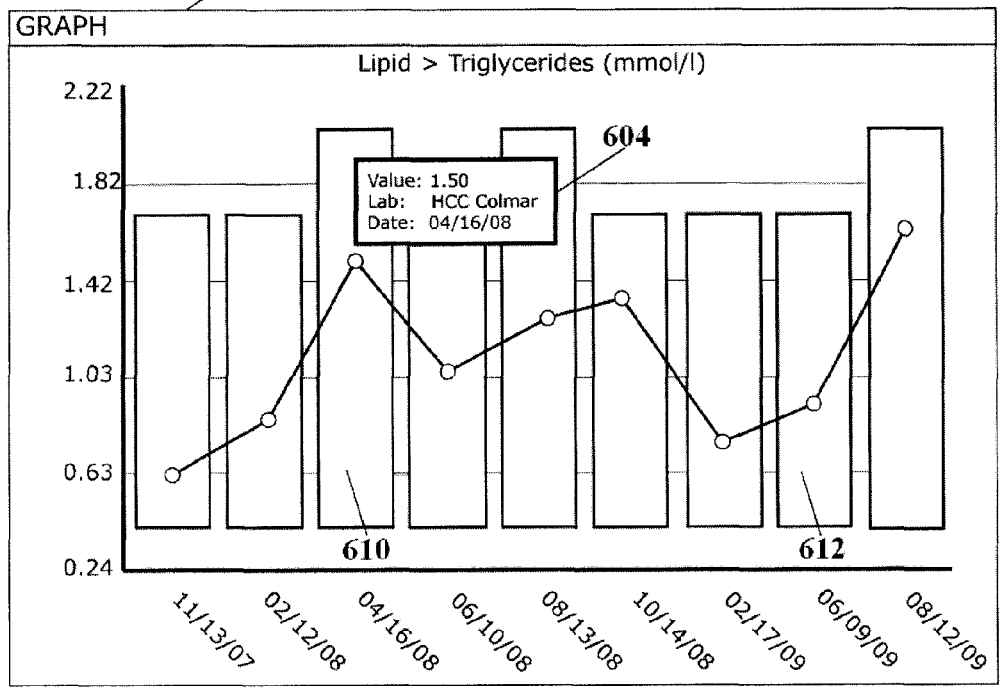
FIGS. 6A and 6B show exemplary graphical results of outputs of correlated lab test data in accordance with embodiments of the present disclosure.
Figure 6B:
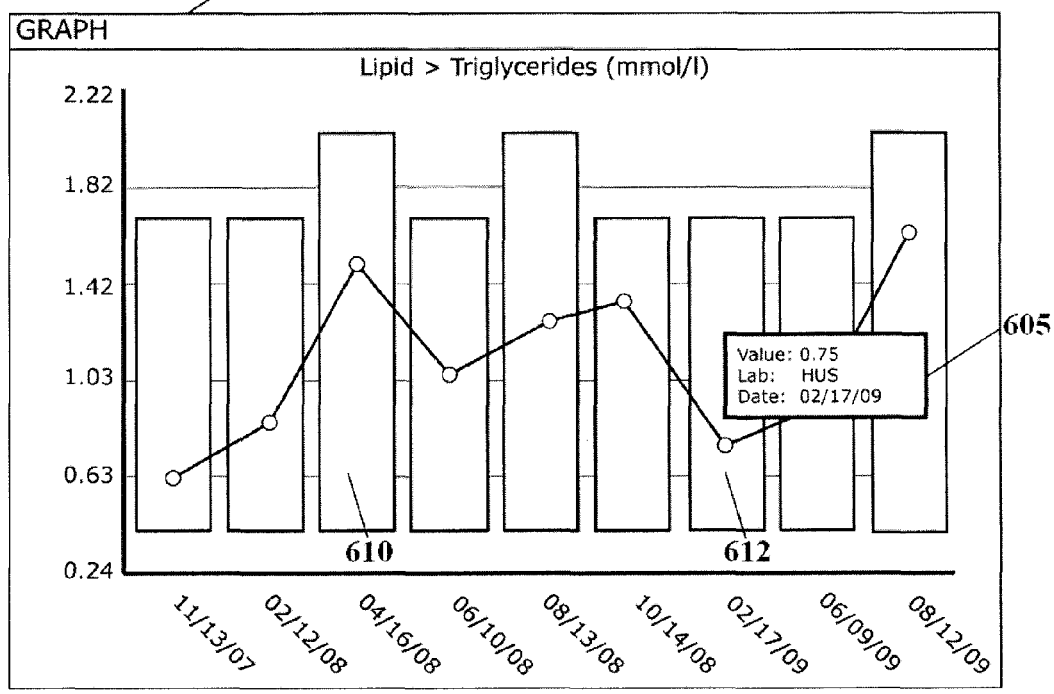

Now referring to FIGS. 6A and 6B, a graphical representation of the data is shown. Again, FIGS. 6A and 6B show the same graphical image in graphs 600 and 601, respectively, but show pop-up indicators 604 and 605, respectively, indicating which data points were received from which laboratory. Graphs 600 and 601 may display a particular lab test over time, thereby providing visualization of trends. Further, the graphical representation can easily show what the laboratories consider normal and/or acceptable values for a particular test. Box 610 represents the normal range for triglycerides as received from HCC Colmar, and box 612 represents the normal range for triglycerides as received from H.U.S. Accordingly, a healthcare provider may note that a particular lab test result was "out of range" for one laboratory, but within range for another laboratory. This allows the healthcare provider to see trends and eliminate discrepancies between laboratories, thereby making diagnosis and/or treatment more efficient and accurate with respect to a particular patient.

Figure 7:
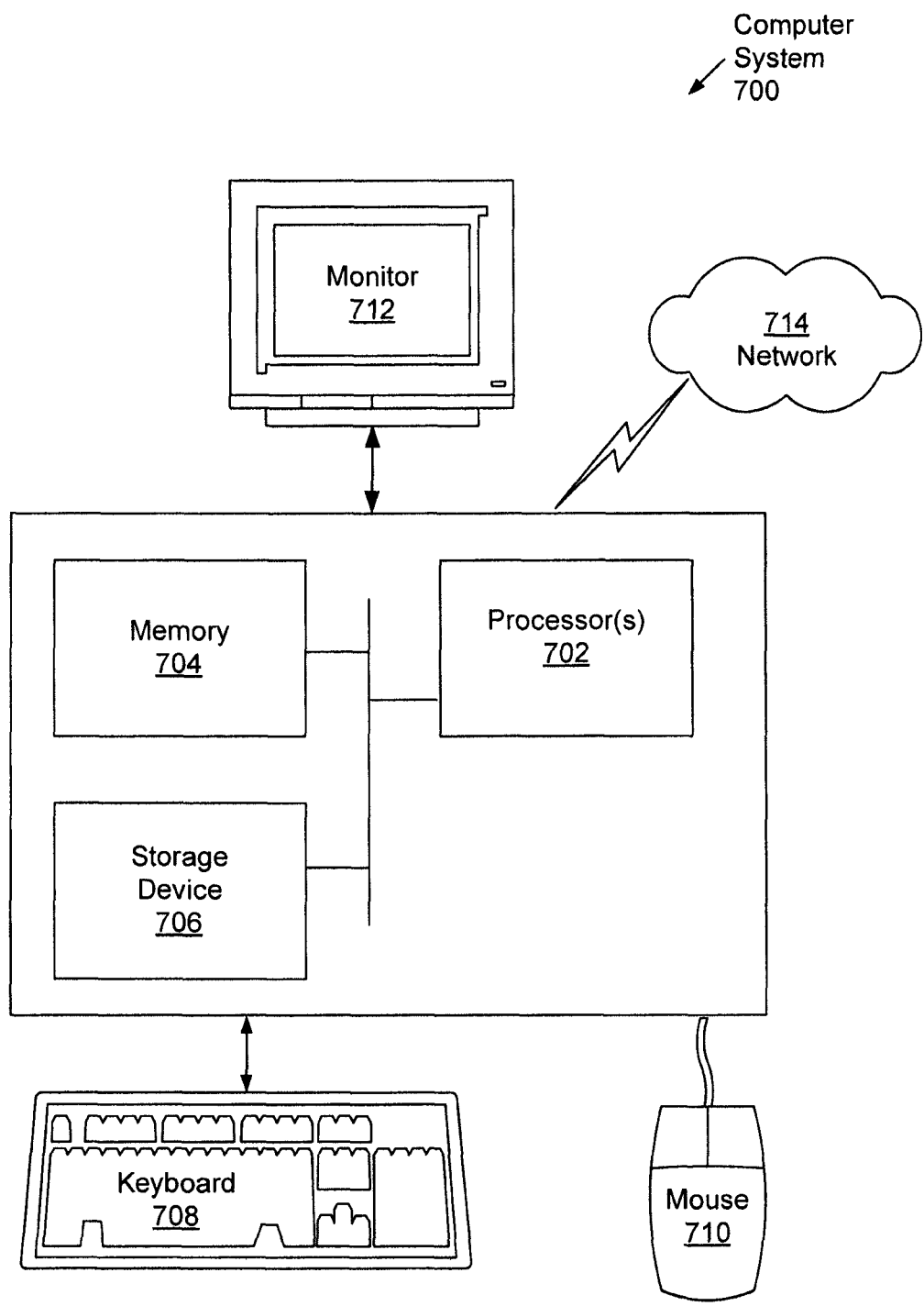
FIG. 7 shows a schematic view of a computer system that may be used in accordance with one or more embodiments of the present disclosure.

Embodiments of the invention may be implemented on virtually any type of computer regardless of the platform being used. For example, as shown in FIG. 7, a computer system 700 includes one or more processor(s) 702 (such as a central processing unit (CPU), integrated circuit, etc.), associated memory 704 (e.g., random access memory (RAM), cache memory, flash memory, etc.), a storage device 706 (e.g., a hard disk, an optical drive such as a compact disk drive or digital video disk (DVD) drive, a flash memory stick, etc.), and numerous other elements and functionalities typical of today's computers (not shown). The computer system 700 may also include input means, such as a keyboard 708, a mouse 710, or a microphone (not shown). Further, the computer system 700 may include output means, such as a monitor 712 (e.g., a liquid crystal display (LCD), a plasma display, or cathode ray tube (CRT) monitor). The computer system (400) may be connected to a network 714 (e.g., a local area network (LAN), a wide area network (WAN), the Internet, or any other type of network) via a network interface connection (not shown). Those skilled in the art will appreciate that many different types of computer systems exist, and the aforementioned input and output means may take other forms. Generally speaking, the computer system 700 includes at least the minimal processing, input, and/or output means necessary to practice embodiments of the invention.

Further, in one or more embodiments of the invention, one or more elements of the aforementioned computer system 700 may be located at a remote location and connected to the other elements over a network. Further, embodiments of the invention may be implemented on a distributed system having a plurality of nodes, where each portion of the invention (e.g., checker 102, parsers 110, translator 108, writer 104, storage unit 106, etc.) may be located on a different node within the distributed system. In one embodiment of the invention, the node corresponds to a computer system. Alternatively, the node may correspond to a processor with associated physical memory. The node may alternatively correspond to a processor or micro-core of a processor with shared memory and/or resources. Further, software instructions in the form of computer readable program code to perform embodiments of the invention may be stored, temporarily or permanently, on a tangible computer readable storage medium, such as a compact disc (CD), a diskette, a tape, punch cards, memory, or any other tangible computer readable storage device.

Advantageously, embodiments disclosed herein provide a service, process, or method of allowing interoperability of lab test data from disparate laboratories, without requiring any changes to be made at the laboratory level. The laboratories may submit lab test data to a central server in any format, and by any means, and a healthcare provider may be able to reconcile the results from a multitude of laboratories.

Moreover, embodiments disclosed here may allow for a general patient ID to be provided, thereby allowing simple joining and referencing of laboratory results over time. Additionally, the patient ID may allow for privacy and protect of a patient's eHR.

Moreover, embodiments of the invention may allow for human intervention to allow the system to learn errors in the provided laboratory data. For example, laboratories may provide and/or send data that is not in compliance with the norms of the standard formats, or not in compliance with the appropriate coding, or errors may exist in the data, etc. The follow examples may be sorted and learned by the system, allowing for a comprehensive analysis and accurate health record.

Non Compliance with Norms
Ex HPRIM physician: the formatted text contains a <<TXT>> segment with an embedded result but is lacking the <<RES>> segment which could be submitted to subsequent analysis.
TEX|tAlbumine . . . : <3 mg/l
instead of|Albumine . . . : <<3 mg/l
RES|Albumine|AL|C|#I3|mg/l||N|F||||
Non Compliance with Coding
A lab can send different coded results for the same final result:
RES|Protéines|UP|C|#I010|g/l|0.0|0.1|N|F||||
or
RES|Protéines|UP|C|#I0.10|g/l|0.0|0.1|N|F||||
means in both cases:
Protéines . . . : <0.10 g/l
Further, two coded lab test results, with the same <<inside>> value, can end into different values.
RES|Protéines|UP|C|#I010|g/l|0.0|0.1|N|F||||
means:
Protéines . . . : <0.10 g/l
or
Protéines . . . : <1.0 g/l
Different Codes for a Single Test
The same lab can use different codes for one single test:
RES|Alpha-foetoprotéine|AFP|N|2.9|kU/1|0.0|7.0|N|F||||

RES|Alpha-foetoprotéine|WAFP|N|2.9|kU/
1|0.0|7.0|N|F||||
RES|Alpha-foetoprotéine|VAFP|N|2.9|kU/
1|0.0|7.0|N|F||||
Means:
Alpha-foetoprotéine . . . : 2.9 kU/1 (inf.à 7.0)

Advantageously, embodiments of the invention provide interoperability between lab test data from disparate laboratories and generates unified, correlated data. Moreover, errors in the data supplied from the disparate laboratories may be reconciled, even if errors exist in the data.

Accordingly, embodiments of the invention provide a utilitarian interoperability selectively oriented to the needs of the end-user, namely the patient, in the form of the central server. Such an approach is fully compliant with the concept of building an individual electronic longitudinal health record, a personal record (DMP, dossier medical personnel), or professional record (CCR, continuous care record), which can be used and efficiently employed by healthcare providers.

Embodiments of the invention allow for the reconciliation of data of a particular patient, sent by lab "X" (any single lab or combination of labs) to the central server, i14y-R, by assigning and employing dictionaries to create a single unified and correlated data set that may allow for the individual electronic longitudinal health record to be formed. As such, lab "X" can be linked to lab "Y" through the i14y-R repository, which may also be connected to one or more additional labs. However, as noted, each lab may employ its own format and/or language, such as differentiation in the reference to red blood cells, as explained above. Although there are generally accepted formats, such as HL7 and HPrim, these are not fully standard, and so other formats may exist that must be entered. Accordingly, at the initial step of parsing, some form of "manual" manipulation for treatment of unknown and/or non-recognized files may be required. As such, a human reviewer may be employed at the parsing stage to manually enter new and/or non-recognized formats. However, the parsing function of the central server may be configured to learn the newly entered formats, thereby, eliminating the necessity of human intervention.

While the disclosure has been presented with respect to a limited number of embodiments, those skilled in the art, having benefit of this disclosure, will appreciate that other embodiments may be devised which do not depart from the scope of the present disclosure. Accordingly, the scope of the invention should be limited only by the attached claims.

What is claimed is:

1. A method for displaying correlated data of a patient, the method comprising:
    storing on at least one digital memory device incoming lab test data of the patient;
    parsing the stored incoming lab test data to determine a first lab test data and a second lab test data of the patient;
    generating first correlated data from the first lab test data comprising a first lab test result and a first lab test normal range;
    generating second correlated data from the second lab test data comprising a second lab test result and a second lab test normal range,
    wherein the first lab test data and the second lab test data represent a particular lab test of a first type;
    generating, for display on a display, a graphical representation of the first lab test normal range and a graphical representation of the first lab test result in a manner such that it is visually apparent whether the first lab test result is within the first lab test normal range; and
    generating, for display on the display, a graphical representation of the second lab test normal range and a graphical representation of the second lab test result in a manner such that it is visually apparent whether the second lab test result is within the second lab test normal range; and
    displaying, on the display, the graphical representation of the first lab test normal range and the graphical representation of the second lab test normal range are displayed using a common value scale and are displayed adjacent one another on the display.

2. The method of claim 1, further comprising:
    parsing the stored incoming lab test data to further determine a third lab test data of the patient;
    generating third correlated data from the third lab test data comprising a third lab test result and a third lab test normal range,
    wherein the third lab test data represent the particular lab test of the first type; and
    generating, for display on the display, a graphical representation of the third lab test normal range and a graphical representation of the third lab test result in a manner such that it is visually apparent whether the third lab test result is within the third lab test normal range;
    displaying, on the display, the graphical representation of the third lab test normal range is displayed using the common value scale and is displayed adjacent one of the graphical representation of the first lab test normal range and the graphical representation of the second lab test normal range.

3. The method of claim 2, further comprising displaying, on the display, a graph having a first axis and a second axis perpendicular to the first axis;
    wherein the common value scale is displayed along the first axis;
    wherein a lab test identification label is displayed along the second axis for each of the first lab test data, the second lab test data, and the third lab test data; and
    wherein the graphical representations of the first lab test normal range, the first lab test result, the second lab test normal range, the second lab test result, the third lab test normal range, and the third lab test result are displayed on the graph in locations corresponding to the common value scale displayed along the first axis and the lab test identification labels displayed along the second axis.

4. The method of claim 3, further comprising displaying, on the display, a line between the graphical representation of the first lab test result and the second lab test result.

5. The method of claim 4, further comprising displaying, on the display, a line between the graphical representation of the second lab test result and the third lab test result.

6. The method of claim 3, wherein the graphical representations of the first, second, and third lab test normal ranges are elongated geometric shapes, and wherein each of the graphical representations of the first, second, and third lab test results are points displayed within a corresponding elongated geometric shape if a result value is within a corresponding normal range and are points displayed outside the corresponding elongated geometric shape if the result value is outside the corresponding normal range.

7. The method of claim 6, further comprising displaying, on the display, a line between the graphical representation of the first lab test result and the second lab test result, and a line between the second lab test result and the third lab test result.

8. The method of claim 3, wherein the lab test identification labels are displayed along the second axis in chronological order according to a date of a corresponding lab test result.

9. The method of claim 2, further comprising displaying, on the display, a line between the graphical representation of the first lab test result and the second lab test result.

10. The method of claim 9, further comprising displaying, on the display, a line between the graphical representation of the second lab test result and the third lab test result.

11. The method of claim 1, further comprising displaying, on the display, a graph having a first axis and a second axis perpendicular to the first axis;
   wherein the common value scale is displayed along the first axis;
   wherein a lab test identification label is displayed along the second axis for each of the first lab test data and the second lab test data; and
   wherein the graphical representations of the first lab test normal range, the first lab test result, the second lab test normal range, and the second lab test result are displayed on the graph in locations corresponding to the common value scale displayed along the first axis and the lab test identification labels displayed along the second axis.

12. The method of claim 11, further comprising displaying, on the display, a line between the graphical representation of the first lab test result and the second lab test result.

13. The method of claim 1, further comprising displaying, on the display, a line between the graphical representation of the first lab test result and the second lab test result.

14. The method of claim 1, wherein the first lab test data and the second lab test data are from different laboratories.

15. A system to display correlated data of a patient, the system comprising:
   a hardware processor;
   a memory operatively connected to the hardware processor;
   a storage device;
   a display; and
   software instructions stored in the memory and comprising functionality to:
      receive, using the hardware processor, first lab test data of the patient in a first received format and second lab test data of the patient in a second received format, wherein the first lab test data comprise a first lab test result and a first lab test normal range, wherein the second lab test data comprise a second lab test result and a second lab test normal range, and wherein the first lab test data and the second lab test data represent a particular lab test of a first type;
      store, on the storage device, the first lab test data and the second lab test data;
      display, on the display, a graphical representation of the first lab test normal range and a graphical representation of the first lab test result in a manner such that it is visually apparent whether the first lab test result is within the first lab test normal range; and
      display, on the display, a graphical representation of the second lab test normal range and a graphical representation of the second lab test result in a manner such that it is visually apparent whether the second lab test result is within the second lab test normal range;
      wherein the graphical representation of the first lab test normal range and the graphical representation of the second lab test normal range are displayed using a common value scale and are displayed adjacent one another on the display.

16. The system of claim 15, wherein the software instructions further comprise functionality to:
   receive, using the hardware processor, third lab test data of the patient in a third received format, wherein the third lab test data comprise a third lab test result and a third lab test normal range, and wherein the third lab test data represent the particular lab test data of the first type;
   store, on the storage device, the third lab test data; and
   display, on the display, a graphical representation of the third lab test normal range and a graphical representation of the third lab test result in a manner such that it is visually apparent whether the third lab test result is within the third lab test normal range;
   wherein the graphical representation of the third lab test normal range is displayed using the common value scale and is displayed adjacent one of the graphical representation of the first lab test normal range and the graphical representation of the second lab test normal range.

17. The system of claim 16, wherein the software instructions further comprise functionality to display, on the display, a graph having a first axis and a second axis perpendicular to the first axis;
   wherein the common value scale is displayed along the first axis;
   wherein a lab test identification label is displayed along the second axis for each of the first lab test data, the second lab test data, and the third lab test data; and
   wherein the graphical representations of the first lab test normal range, the first lab test result, the second lab test normal range, the second lab test result, the third lab test normal range, and the third lab test result are displayed on the graph in locations corresponding to the common value scale displayed along the first axis and the lab test identification labels displayed along the second axis.

18. The system of claim 17, wherein the software instructions further comprise functionality to display, on the display, a line between the graphical representation of the first lab test result and the second lab test result.

19. The system of claim 18, wherein the software instructions further comprise functionality to display, on the display, a line between the graphical representation of the second lab test result and the third lab test result.

20. The system of claim 17, wherein the graphical representations of the first, second, and third lab test normal ranges are elongated geometric shapes, and wherein each of the graphical representations of the first, second, and third lab test results are points displayed within a corresponding elongated geometric shape if a result value is within a corresponding normal range and are points displayed outside the corresponding elongated geometric shape if the result value is outside the corresponding normal range.

21. The system of claim 20, further comprising displaying, on the display, a line between the graphical representation of the first lab test result and the second lab test result, and a line between the second lab test result and the third lab test result.

22. The system of claim 17, wherein the lab test identification labels are displayed along the second axis in chronological order according to a date of a corresponding lab test result.

23. The system of claim 16, wherein the software instructions further comprise functionality to display, on the display, a line between the graphical representation of the first lab test result and the second lab test result.

24. The system of claim 23, wherein the software instructions further comprise functionality to display, on the display, a line between the graphical representation of the second lab test result and the third lab test result.

25. The system of claim 16, wherein the first lab test data is stored on the storage device in the first received format and the second lab test data is stored on the storage device in the second received format, and wherein the software instructions further comprise functionality to convert, using the hardware processor, the first lab test data into a unified format and the second lab test data into the unified format.

26. The system of claim 25, wherein the third lab test data is stored on the storage device in the third received format, and wherein the software instructions further comprise functionality to convert, using the hardware processor, the third lab test data into the unified format.

27. The system of claim 15, wherein the software instructions further comprise functionality to display, on the display, a graph having a first axis and a second axis perpendicular to the first axis;
   wherein the common value scale is displayed along the first axis;
   wherein a lab test identification label is displayed along the second axis for each of the first lab test data and the second lab test data; and
   wherein the graphical representations of the first lab test normal range, the first lab test result, the second lab test normal range, and the second lab test result are displayed on the graph in locations corresponding to the common value scale displayed along the first axis and the lab test identification labels displayed along the second axis.

28. The system of claim 27, wherein the software instructions further comprise functionality to display, on the display, a line between the graphical representation of the first lab test result and the second lab test result.

29. The system of claim 15, wherein the software instructions further comprise functionality to display, on the display, a line between the graphical representation of the first lab test result and the second lab test result.

30. The system of claim 15, wherein the first lab test data and the second lab test data are from different laboratories.

31. The system of claim 15, wherein the first lab test data is stored on the storage device in the first received format and the second lab test data is stored on the storage device in the second received format, and wherein the software instructions further comprise functionality to convert, using the hardware processor, the first lab test data into a unified format and the second lab test data into the unified format.

32. A system to display correlated data of a patient, the system comprising:
   a hardware processor;
   a memory operatively connected to the hardware processor;
   a storage device;
   a display; and
   software instructions stored in the memory and comprising functionality to:
      receive, using the hardware processor, first lab test data of the patient in a first received format, second lab test data of the patient in a second received format, and third lab test data of the patient in a third received format, wherein the first lab test data comprise a first lab test result and a first lab test normal range, wherein the second lab test data comprise a second lab test result and a second lab test normal range, and the third lab test data comprise a third lab test result and a third lab test normal range, wherein the first lab test data, the second lab test data, and the third lab test data represent a particular lab test of a first type;
      store, on the storage device, the first lab test data in the first received format, the second lab test data in the second received format, and the third lab test data in the third received format,
      if the first received format of the first lab test data is not in a desired format, then convert, using the hardware processor, the first lab test data into the desired format;
      if the second received format of the second lab test data is not in the desired format, then convert, using the hardware processor, the second lab test data into the desired format;
      if the third received format of the third lab test data is not in the desired format, then convert, using the hardware processor, the third lab test data into the desired format;
      reconcile a test type name of the first lab test data, a test type name of the second lab test data, and a test type name of the third lab test data to a first common test name;
      display, on the display, a table comprising the first lab test result, the second lab test result, and the third lab test result, wherein each of the first lab test result, the second lab test result, and the third lab test result is associated on a first axis with a chronological date, and on a second axis with the first common test name; and
      when one of the first lab test result, the second lab test result, and the third lab test result is selected by a user using a pointing device, display, on the display, a pop-up comprising the normal range corresponding to the selected lab test result.

33. The system of claim 32, wherein the first lab test result, the second lab test result, and the third lab test result are displayed using an indicia that visually differentiates a characteristic amongst the lab test results.

34. The system of claim 33, wherein the indicia indicates at least one of an origination of the lab test result, whether the lab test result is above or below a corresponding normal range, and whether the lab test result is a most recent result of the patient.

35. The system of claim 33, wherein the indicia is at least one of font, italics, brackets, and underlining.

36. The system of claim 32, the software instructions further comprising functionality to:
   receive, using the hardware processor, fourth lab test data of the patient in a fourth received format, fifth lab test data of the patient in a fifth received format, and sixth lab test data of the patient in a sixth received format, wherein the fourth lab test data comprise a fourth lab test result and a fourth lab test normal range, wherein the fifth lab test data comprise a fifth lab test result and a fifth lab test normal range, and the sixth lab test data comprise a sixth lab test result and a sixth lab test normal range,
      wherein the fourth lab test data, the fifth lab test data, and the sixth lab test data represent a particular lab test of a second type;
   store, on the storage device, the fourth lab test data in the fourth received format, the fifth lab test data in the fifth received format, and the sixth lab test data in the sixth received format,
   if the fourth received format of the fourth lab test data is not in a desired format, then convert, using the hardware processor, the fourth lab test data into the desired format;
   if the fifth received format of the fifth lab test data is not in the desired format, then convert, using the hardware processor, the fifth lab test data into the desired format;
   if the sixth received format of the sixth lab test data is not in the desired format, then convert, using the hardware processor, the sixth lab test data into the desired format;

reconcile a test type name of the fourth lab test data, a test type name of the fifth lab test data, and a test type name of the sixth lab test data to a second common test name;

display, on the table, the fourth lab test result, the fifth lab test result, and the sixth lab test result, wherein each of the fourth lab test result, the fifth lab test result, and the sixth lab test result is associated on the first axis with a chronological date, and on the second axis with the second common test name; and when one of the fourth lab test result, the fifth lab test result, and the sixth lab test result is selected by a user using a pointing device, display, on the display, a pop-up comprising the normal range corresponding to the selected lab test result.

* * * * *